United States Patent
Krebs et al.

(10) Patent No.: US 11,766,158 B2
(45) Date of Patent: Sep. 26, 2023

(54) VACUUM CLEANER

(71) Applicant: BISSELL Inc., Grand Rapids, MI (US)

(72) Inventors: Alan J. Krebs, Pierson, MI (US); Thomas K. Ankney, Grand Rapids, MI (US)

(73) Assignee: BISSELL Inc., Grand Rapids, MI (US)

( * ) Notice: Subject to any disclaimer, the term of this patent is extended or adjusted under 35 U.S.C. 154(b) by 366 days.

(21) Appl. No.: 17/089,068

(22) Filed: Nov. 4, 2020

(65) Prior Publication Data

US 2021/0045603 A1   Feb. 18, 2021

Related U.S. Application Data

(63) Continuation of application No. 16/116,040, filed on Aug. 29, 2018, now Pat. No. 10,827,892.

(60) Provisional application No. 62/556,618, filed on Sep. 11, 2017.

(51) Int. Cl.
| | |
|---|---|
| *A47L 9/18* | (2006.01) |
| *A61L 9/14* | (2006.01) |
| *B01D 47/06* | (2006.01) |
| *A47L 9/28* | (2006.01) |
| *A47L 9/16* | (2006.01) |

(52) U.S. Cl.
CPC ............... *A47L 9/183* (2013.01); *A47L 9/16* (2013.01); *A47L 9/2836* (2013.01); *A47L 9/2868* (2013.01); *A61L 9/14* (2013.01); *B01D 47/06* (2013.01); *A61L 2209/132* (2013.01)

(58) Field of Classification Search
CPC ..... A47L 5/30; A47L 5/36; A47L 9/16; A47L 9/1608; A47L 9/183; A47L 9/2836; A47L 9/2857; A47L 9/2868; A61L 2209/132; A61L 9/14; B01D 47/06
See application file for complete search history.

(56) References Cited

U.S. PATENT DOCUMENTS

| | | | |
|---|---|---|---|
| 2,648,396 | A | 8/1953 | Kirby |
| 6,419,122 | B1 | 7/2002 | Chown |
| 9,888,821 | B2 * | 2/2018 | Scholten ................. A47L 13/38 |
| 2003/0140444 | A1 | 7/2003 | Soejima |
| 2004/0013583 | A1 | 1/2004 | Burkhardt |
| 2005/0000054 | A1 | 1/2005 | Ninomiya |
| 2005/0160553 | A1 * | 7/2005 | Gregory ................. A47L 7/0038 15/320 |

(Continued)

FOREIGN PATENT DOCUMENTS

| | | |
|---|---|---|
| CN | 202942035 U | 5/2013 |
| CN | 103169428 A | 6/2013 |

(Continued)

OTHER PUBLICATIONS

JP-09262197-A—English Machine Translation (Year: 1997).*

(Continued)

*Primary Examiner* — Marc Carlson
(74) *Attorney, Agent, or Firm* — McGarry Bair PC

(57) ABSTRACT

A vacuum cleaner includes an odor neutralizer and dust plume abatement system. The odor neutralizer and dust plume abatement system delivers a mist to a working air path of the vacuum cleaner, such as at or upstream of a working air treatment assembly defining a portion of the working air path.

20 Claims, 10 Drawing Sheets

(56) References Cited

U.S. PATENT DOCUMENTS

| | | | |
|---|---|---|---|
| 2006/0179599 A1* | 8/2006 | Miner | A47L 11/34 15/385 |
| 2006/0225242 A1* | 10/2006 | Oh | A61L 9/14 422/292 |
| 2010/0037915 A1* | 2/2010 | Johnson | A47L 11/4088 134/6 |
| 2015/0223660 A1* | 8/2015 | Scholten | A47L 11/4086 261/78.2 |
| 2018/0125322 A1* | 5/2018 | Scholten | A47L 7/0004 |
| 2018/0333736 A1* | 11/2018 | Krebs | A47L 5/365 |
| 2019/0075989 A1* | 3/2019 | Krebs | A47L 5/30 |
| 2021/0045603 A1* | 2/2021 | Krebs | A47L 9/2857 |

FOREIGN PATENT DOCUMENTS

| | | | |
|---|---|---|---|
| DE | 3740517 A1 | * | 6/1989 |
| DE | 3740517 A1 | | 6/1989 |
| JP | 5239730 B2 | | 9/1993 |
| JP | 08256961 A | * | 10/1996 |
| JP | H08256961 A | | 10/1996 |
| JP | 09262197 A | | 10/1997 |
| JP | 09262197 A | * | 10/1997 |
| JP | H09262197 A | | 10/1997 |
| JP | H092621987 A | | 10/1997 |
| JP | 2006102008 A2 | | 4/2006 |
| JP | 2011041710 A | * | 3/2011 |
| JP | 2011136010 A | | 7/2011 |
| JP | 2011156220 A | * | 8/2011 |
| JP | 2011156220 A | | 8/2011 |
| JP | 4978675 B2 | | 7/2012 |

OTHER PUBLICATIONS

Intellectual Property Office, Combined Search and Examination Report under Sections 17 and 18(3), dated Feb. 4, 2021, 6 pages, South Wales, NP.

Evans, Rhodri, Patents Act 1997: Search Report under Section 17(5), 5 pgs., dated Feb. 18, 2019 South Wales.

* cited by examiner

VACUUM CLEANER

CROSS-REFERENCE TO RELATED APPLICATION(S)

This application is a continuation of U.S. patent application Ser. No. 16/116,040, filed Aug. 29, 2018, now U.S. Pat. No. 10,827,892, issued Nov. 10, 2020, which claims the benefit of U.S. Provisional Patent Application No. 62/556,618, filed Sep. 11, 2017, all of which are incorporated herein by reference in their entirety.

BACKGROUND

Vacuum cleaners can be embodied as upright units or portable, hand-carriable units. In some instances, a vacuum cleaner can be reconfigurable between an upright cleaning mode and a lift-off mode in which a smaller pod or hand-carriable unit is removed from the vacuum cleaner for use in a cleaning operation.

Vacuum cleaners employ a variety of dirt separators to remove dirt and other debris from a working airstream. Some dirt separators use one or more frusto-conical-shaped separator(s) and others use high-speed rotational motion of the air/dirt to separate the dirt by centrifugal force. Before exiting the dirt separator, the working air may flow through an exhaust grill.

A dirt cup can be provided for collecting the removed dirt from the working airstream, and can be separate from or integral with the dirt separator. In vacuum cleaners where the dirt separator and collector are separate, the dirt cup can be removable from the vacuum cleaner for emptying collected dirt, without removing the dirt separator. In vacuum cleaners where the dirt separator and collector are integral, the entire separator/collector assembly can be removable from the vacuum cleaner for emptying collected dirt. In this case, a bottom wall of the assembly often serves as a dirt door, and is provided with a release mechanism for opening the dirt door to empty the accumulated contents.

Dirt separators may not remove all dirt from the working airstream. Furthermore, swirling air currents in the dirt cup may cause separated dirt to be re-entrained in the working airstream. Still further, when removing the dirt cup from the vacuum cleaner and emptying the accumulated contents, plumes of fine dust may be released from the dirt cup.

BRIEF DESCRIPTION

An aspect of the present disclosure includes a surface cleaning apparatus having a housing, a working air path through the housing comprising a dirty air inlet and a clean air outlet, a working air treatment assembly defining a portion of the working air path, a suction source defining a portion of the working air path and in fluid communication with the working air treatment assembly, and an odor neutralizer and dust plume abatement system configured to dispense a mist into the working air path, the system comprising a receiver including a mount for receiving an aerosol dispenser, the receiver in fluid communication with the working air path at or upstream of the working air treatment assembly.

DETAILED DESCRIPTION

Figure 1:
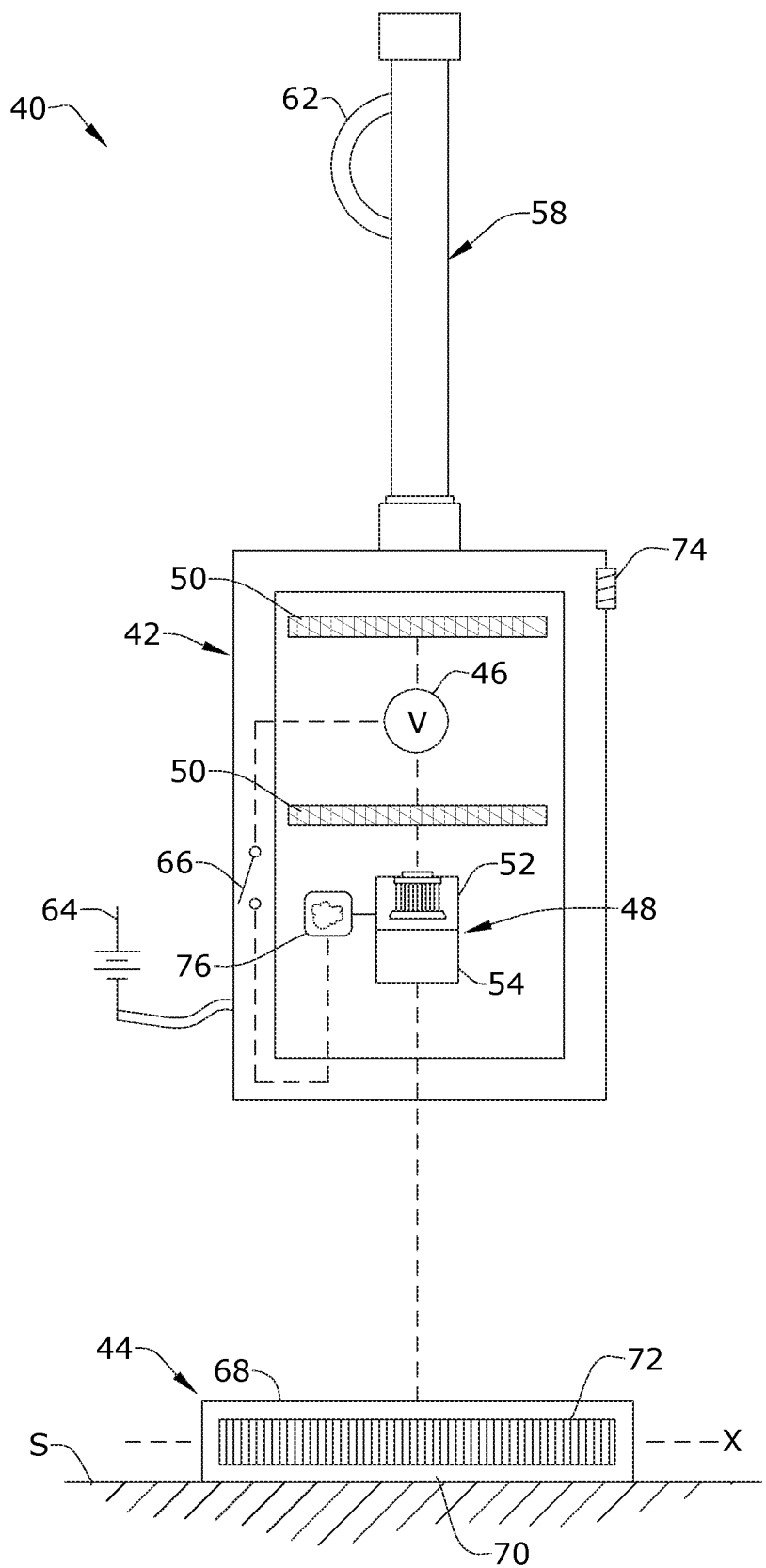
FIG. 1 is a schematic view of a vacuum cleaner having an odor neutralizer and dust plume abatement system according to an aspect of the present disclosure.

The present disclosure relates to vacuum cleaners. In one of its aspects, the present disclosure relates to a vacuum cleaner with a system for neutralizing odors. In one of its aspects, the present disclosure relates to a vacuum cleaner with a system for dust abatement. In yet another aspect, the present disclosure relates to a vacuum cleaner with a combined system for neutralizing odors and dust abatement.

A vacuum cleaner according to one aspect of the present disclosure includes an odor neutralizer and dust plume abatement system. The odor neutralizer and dust plume abatement system can neutralize odors and abate dust plumes within a working air path of the vacuum cleaner. A working air path of a vacuum cleaner may be defined between a dirty air inlet and a clean air outlet of the vacuum cleaner, and may include one or more of a suction source, such as a vacuum motor, working air treatment assembly, which can include a dirt separation/collection module or debris removal assembly, filters, and/or conduits defining the working air path. The odor neutralizer and dust plume abatement system can be integrated with working air treatment assembly for treating the portion of the working air path defined by the working air treatment assembly.

In one aspect, the odor neutralizer and dust plume abatement system can include a mist generator and a valve configured to control the flow of mist into the working air path of the vacuum cleaner, at or upstream of the working air treatment assembly.

In another aspect, the odor neutralizer and dust plume abatement system can include an aerosol dispenser configured to dispense a spray of aerosol mist into the working air path of the vacuum cleaner, at or upstream of the working air treatment assembly.

A vacuum cleaner according to another aspect of the present disclosure includes a dirt separation/collection module and an odor neutralizer and dust plume abatement system with a piezoelectric mist generator that generates mist and a mist chamber into which the mist is selectively dispensed, where the mist chamber is in fluid communication with the dirt separation/collection module.

A vacuum cleaner according to another aspect of the present disclosure includes a suction source, a dirt separation/collection module and an odor neutralizer and dust plume abatement system with a mist generator that generates mist, a mist chamber into which the mist is selectively dispensed, where the mist chamber is in fluid communication with the dirt separation/collection module, and a valve between the mist chamber and dirt separation/collection module configured to be opened temporarily while the suction source is energized so the mist in the mist chamber can be pulled into the dirt separation/collection module by the partial vacuum generated by the suction source.

A vacuum cleaner according to another aspect of the present disclosure includes a dirt separation/collection module and an odor neutralizer and dust plume abatement system with an aerosol dispenser mounted to a receiver on the vacuum cleaner in fluid communication with the dirt separator/collection module.

A vacuum cleaner according to another aspect of the present disclosure includes a dirt separation/collection module and an odor neutralizer and dust plume abatement system with an aerosol dispenser mounted to a receiver on the vacuum cleaner in fluid communication with the dirt separator/collection module and a manual or automatic actuator for selectively dispensing from the aerosol dispenser.

FIG. 1 is a schematic view of a vacuum cleaner 40 according to a first aspect of the present disclosure. The vacuum cleaner includes a vacuum collection system for creating a partial vacuum to suck up dirt (which, as used herein, may include dirt, dust, soil, hair, and other debris) from a surface to be cleaned and collecting the removed debris in a collection space provided on the vacuum cleaner 40 for later disposal. The vacuum collection system can include a working air path through the vacuum cleaner. The vacuum cleaner further includes an odor neutralizer and dust plume abatement system 76 for neutralizing odors and abating dust plumes within the working air path of the vacuum cleaner.

The vacuum cleaner 40 may be in the form of an upright vacuum cleaner, a stick-type vacuum cleaner, a canister vacuum cleaner having a floor nozzle or a hand-held accessory tool connected to a canister or other portable device by a vacuum hose or conduit, a vacuum cleaner having a detachable pod with a hand-carried mode of operation, a hand-held vacuum cleaner, or an autonomous robotic sweeping or vacuum cleaning device. Additionally, in some aspects of the present disclosure the vacuum cleaner can have fluid delivery capability for applying a fluid, including liquid and/or steam, to the surface to be cleaned, and/or fluid extraction capability for extracting fluid from the surface to be cleaned.

The vacuum cleaner 40 is shown herein as an upright or stick-type vacuum cleaner, with a housing including an upper unit 42 coupled with a foot or base 44 adapted to be moved over a surface to be cleaned S. The upper unit 42 can be pivotally mounted to the base 44 for movement between an upright storage position, shown in FIG. 1, and a reclined use position (not shown) by a coupling joint. The coupling joint can be a single axis or multi-axis pivot coupling. The vacuum cleaner 40 can be provided with a detent mechanism, such as a pedal pivotally mounted to the base 44, for selectively releasing the upper unit 42 from the storage position to the use position. The details of such a detent pedal are known in the art, and will not be discussed in further detail herein.

The working air path through the housing of the vacuum cleaner 40 may include a dirty air inlet and a clean air outlet. The dirty air inlet may be defined by a suction nozzle inlet 70 in the base 44. In addition, the vacuum collection system may include one or more of a suction source, one example of which includes a suction motor 46, in fluid communication with the suction nozzle inlet 70 for generating a working airstream, and a working air treatment assembly 48 for removing and collecting debris from the working airstream for later disposal, portions of which can define the working air path through the housing. The clean air outlet can be defined by an exhaust opening 74 downstream of the suction motor 46.

In the illustrated example, the suction motor 46 and treatment assembly 48 are provided on the upper unit 42, although other locations are possible. The upper unit 42 further includes a handle 58 to facilitate movement of the vacuum cleaner 40 by a user. The handle 58 may further include a hand grip 62 at one end that can be used for maneuvering the vacuum cleaner over a surface to be cleaned. While not shown, at least a portion of the working air pathway between the suction nozzle inlet 70 and the treatment assembly 48 can be formed by a vacuum hose that can be selectively disconnected from fluid communication with the suction nozzle inlet 70 for above-the-floor cleaning.

In one configuration illustrated herein, the treatment assembly 48 can include a dirt separator in the form of a cyclone separator 52 for separating contaminants from a working airstream and a dirt collector in the form of a removable dirt cup 54 for receiving and collecting the separated contaminants from the cyclone separator 52. In another configuration, the treatment assembly 48 can include an integrally formed cyclone separator 52 and dirt collector, with the dirt collector being provided with a structure, such as a bottom-opening debris door, for contaminant disposal. Furthermore, the cyclone separator 52 can have a single cyclonic separation stage as shown, or multiple stages. Likewise, the dirt cup 54 can have a single collection space as shown, or multiple collection spaces.

It is understood that other types of treatment assemblies 48 can be used, such as a centrifugal separator, a bulk separator, a filter bag, or a water-bath separator. The upper unit 42 can also be provided with one or more additional filters 50 upstream or downstream of the treatment assembly 48 and/or the suction motor 46, and/or within the treatment assembly 48.

The suction motor 46 is provided in fluid communication with the treatment assembly 48, and can be positioned downstream or upstream of treatment assembly 48. The suction motor 46 can be electrically coupled to a power source 64, such as a battery or by a power cord plugged into a household electrical outlet. A power switch 66 disposed between the suction motor 46 and the power source 64 can be selectively closed by the user upon pressing a power button or other actuator on the housing of the vacuum cleaner, thereby activating the suction motor 46. As shown herein, the suction motor 46 is downstream of the treatment assembly 48; alternatively, the suction motor 46 can be upstream of the treatment assembly 48.

The suction nozzle inlet 70 can be provided on the floor cleaning head or base 44 adapted to move over the surface to be cleaned. The base 44 is in fluid communication with the suction motor 46 for engaging and cleaning a surface to be cleaned S. The base 44 includes a base housing 68 having the suction nozzle inlet 70 at least partially disposed on the underside and in front of the base housing 68.

An agitator 72 can be provided adjacent to the suction nozzle inlet 70 for agitating the surface to be cleaned S so that the debris is more easily ingested into the working air path. The agitator 72 illustrated herein is a rotatable brushroll positioned within the base 44 adjacent the suction nozzle inlet 70 for rotational movement about an axis X. Some other examples of agitators include, but are not limited to, dual horizontally-rotating brushrolls, one or more vertically-rotating brushrolls, or a stationary brush.

The odor neutralizer and dust plume abatement system 76 is configured to dispense a mist into the working air path of the vacuum cleaner 40. The mist can, for example, be an atomized mist of liquid, a nebulized mist of liquid, a vaporized mist of liquid, or an aerosol mist of liquid. As used herein, the term "mist" encompasses mist, vapor and fog. As used herein, the term "aerosol mist" encompasses suspensions of fine solid particles or liquid droplets in a gas.

The mist can be dispensed at various locations along the working air path, but may be advantageously dispensed into the treatment assembly 48, as shown in the illustrated example. The mist can neutralize odors within the treatment assembly 48 by reacting with odorous compounds to form odorless or reduced odor compounds, and can abate dust plumes within the working air path of the vacuum cleaner 40 by agglomerating the accumulated contents of the dirt collector 54.

The system 76 can be electrically coupled to the power source 64 of the vacuum cleaner 40, or to its own separate supply of power, such as a battery.

The system 76 can be configured for manual or automated actuation. For a manual system 76, a user can manually actuate the system 76 to dispense mist into the treatment assembly 48 in an on-demand basis. For an automated system 76, the system 76 can be automated for automatic operation during operation of the vacuum cleaner 40. For example, the system 76 can be operated while the suction motor 46 is energized to dispense mist into the treatment assembly 48 during a cleaning operation.

The system 76 can be configured for passive or active mist dispensing. In one example of passive mist dispensing, the system 76 can utilize the partial vacuum generated by the suction motor 46 in the working air path to dispense the mist. While the suction motor 46 is energized, mist from the system 76 can be pulled into the treatment assembly 48 by the partial vacuum generated by the suction source. In one example of active mist dispensing, the system 76 can be configured for a pressurized dispensing of mist, such as by using a propellant under pressure or a pump. In another example of active mist dispensing, the system 76 can have a fan separate from the suction source for blowing or pulling the mist into the treatment assembly 48.

The vacuum cleaner 40 can be used to effectively clean the surface to be cleaned S by removing debris (which may include dirt, dust, soil, hair, and other debris) from the surface to be cleaned S in accordance with the following method. The sequence of steps discussed is for illustrative purposes only and is not meant to limit the method in any way as it is understood that the steps may proceed in a different logical order, additional or intervening steps may be included, or described steps may be divided into multiple steps, without detracting from the present disclosure.

To perform vacuum cleaning, the suction motor 46 is coupled to the power source 64 and draws in debris-laden air through the suction nozzle inlet 70 and into the treatment assembly 48 where the debris is substantially separated from the working air. The air flow then passes through the suction motor 46, and through any optional filters 50 positioned upstream and/or downstream from the suction motor 46, prior to being exhausted from the vacuum cleaner 40. During vacuum cleaning, the agitator 72 can agitate debris on the surface to be cleaned S so that the debris is more easily ingested into the suction nozzle inlet 70. Also during vacuum cleaning, the odor neutralizer and dust plume abatement system 76 can neutralize odors and abate dust plumes within the working air path of the vacuum cleaner 40 by dispensing mist into the treatment assembly 48.

After vacuum cleaning, the treatment assembly 48 can be emptied of debris. Likewise, the optional filters 50 can periodically be cleaned or replaced. Likewise, a liquid source of the odor neutralizer and dust plume abatement system 76 can optionally be periodically be refilled or replaced.

Figure 2:
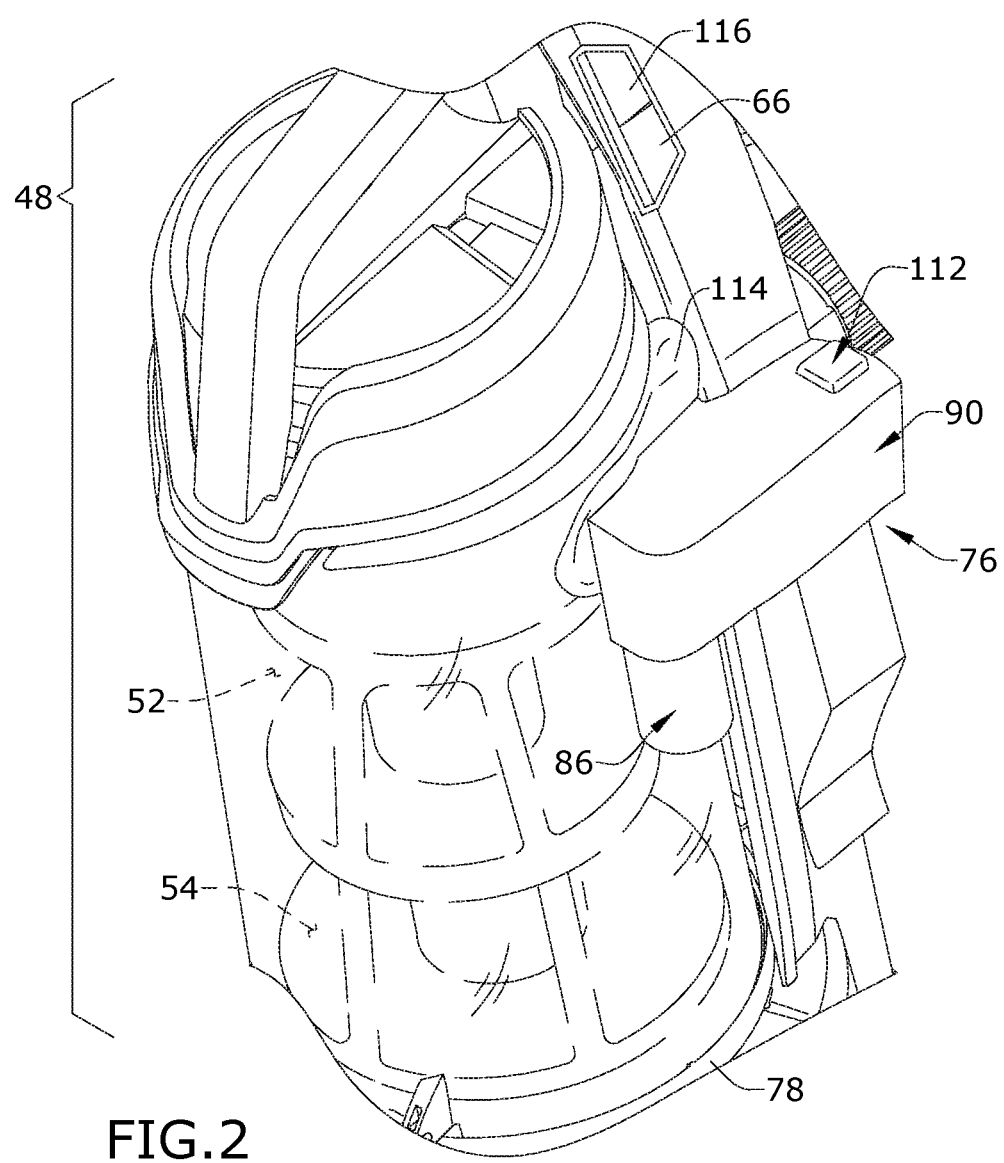
FIG. 2 is a perspective view of a portion of a vacuum cleaner having an odor neutralizer and dust plume abatement system according to another aspect of the present disclosure.
Figure 3:
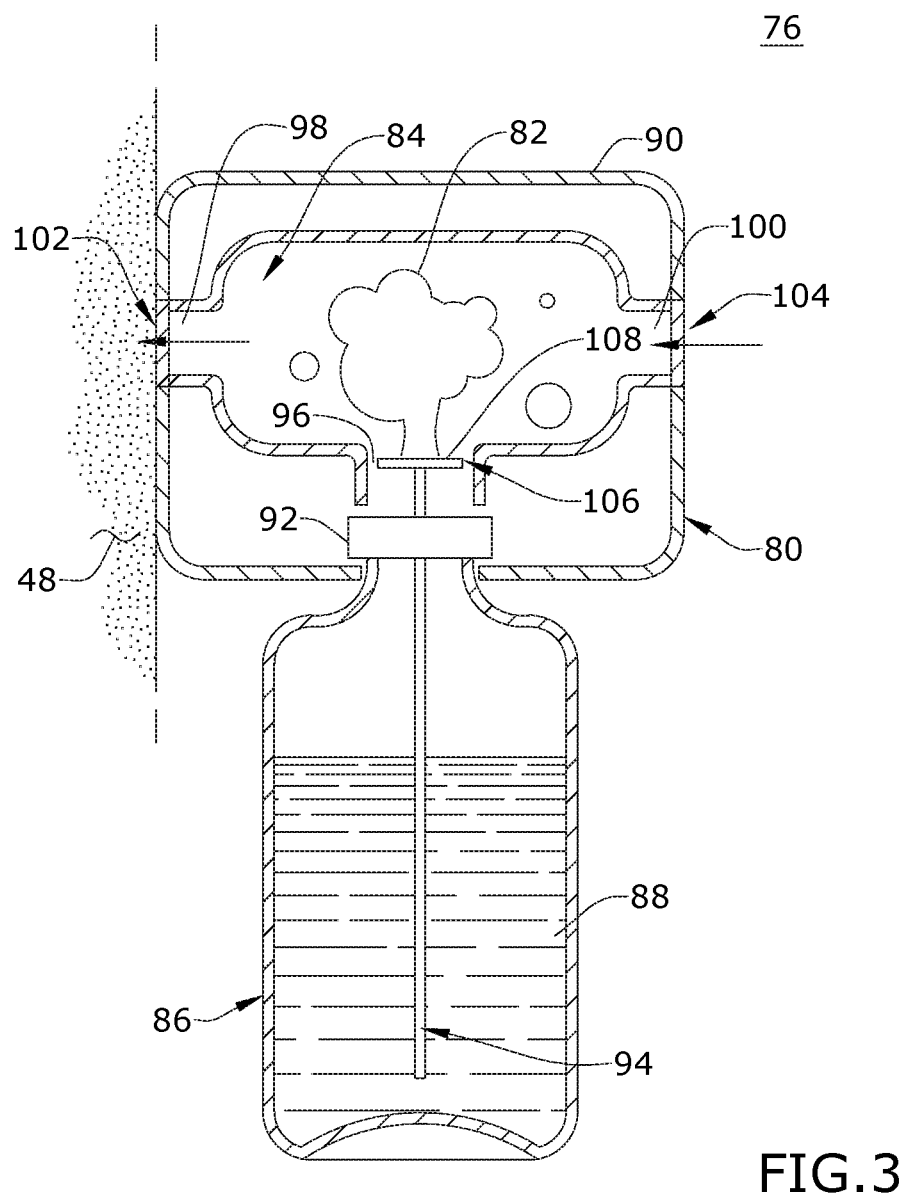
FIG. 3 is a schematic sectional view through a portion of the system of FIG. 2.

FIGS. 2-3 illustrate a second example of a vacuum cleaner 40 having an odor neutralizer and dust plume abatement system 76. The vacuum cleaner 40 may include the same features of the vacuum cleaner 40 of the first example described above with respect to FIG. 1, and is described using the same reference numerals for like elements for the sake of brevity.

In the illustrated example, the dirt separator 52 and dirt collector 54 are integral, and the entire treatment assembly 48 can be removable from the vacuum cleaner 40 for emptying collected dirt. A bottom wall of the assembly 48 includes a dirt door 78, and the treatment assembly 48 is provided with a release mechanism for opening the dirt door 78 to empty the accumulated contents. Furthermore, the odor neutralizer and dust plume abatement system 76 can be separate from the treatment assembly 48 such that when the treatment assembly 48 is removed from the vacuum cleaner 40, the system 76 remains with the vacuum cleaner 40, or may be integral with the treatment assembly 48 such that when the treatment assembly 48 is removed from the vacuum cleaner 40, the system 76 is removed as well.

With reference to FIG. 3, the odor neutralizer and dust plume abatement system 76 of the second example includes a mist generator 80 that generates mist 82 and a mist chamber 84 into which the mist 82 is selectively dispensed, where the mist chamber 84 is in fluid communication with the treatment assembly 48. During operation, the mist generator 80 generates mist 82, which is transferred into the mist chamber 84 for eventual ingestion into the treatment assembly 48. The system 76 is configured to distribute the mist 82, which may be an atomized solution, into the treatment assembly 48 to eliminate or neutralize odors within the treatment assembly 48, prevent dust plumes upon emptying, and improve separation.

The system 76 can further include a liquid reservoir 86 mountable to the vacuum cleaner 40 in fluid communication with the mist generator 80. The liquid reservoir 86 is adapted to hold a quantity of liquid solution 88. The liquid reservoir 86 can be refillable or replaceable. A refillable liquid reservoir can be removable for refilling the reservoir, and then reattached after refilling. A replaceable liquid reservoir can be a disposable or consumable liquid reservoir that is disposed of when empty and replaced with a new, full reservoir.

The liquid solution 88 stored in the liquid reservoir 86 may be water or a mixture including water and one or more treating agents. Treating agents can include, but are not limited to, odor eliminators, sanitizers, stain removers, odor removers, deodorizers, fragrances, or any combination thereof. In one example, an odor remover solution can include a mixture of polypropylene carbonate, a surfactant and a fragrance.

The system 76 can further include a housing 90 enclosing the mist generator 80 and having a receiver 92 for mounting the liquid reservoir 86 on the housing 90. The receiver 92 can further include a seal (not shown) for preventing leakage of the liquid solution 88 and mist, as well as a mechanical coupling (not shown) for securely mounting the reservoir 86 to the receiver 92. Examples of a mechanical coupling can include a bayonet interface, threaded couplings, keyed couplings, and other quick coupling mechanisms, suitable examples of which are more fully disclosed in U.S. Pat. No. 9,615,703, issued Apr. 11, 2017, which is incorporated herein by reference in its entirety. The housing 90 further encloses the mist chamber 84, which is in fluid communication with the treatment assembly 48.

A wick 94 is provided in the liquid reservoir 86 and is in register with the mist generator 80. The wick 94 can define a fluid conduit configured to transfer liquid solution from the liquid reservoir 86 to the mist generator 80, and can more specifically include an absorbent material for transferring solution 88 from the liquid reservoir 86 to the mist generator 80 by capillary action. Some examples of suitable wick material include felt, porous thermoplastic material such as polyethylene (PE), or synthetic thermoplastic polymer fibers such as polyethylene/polyester (PE/PET) fiber. Because the wick 94 transfers the liquid solution 88 by capillary action, the liquid reservoir 86 can be provided below the mist generator 80, and the liquid solution 88 can be transferred to the mist generator 80 regardless of the orientation of the liquid reservoir 86; for example, when the vacuum cleaner 40 is in an upright position or when the vacuum cleaner 40 is in a reclined position.

As illustrated, the mist chamber 84 includes at least a mist chamber inlet 96 and a mist chamber outlet 98 between the mist chamber 84 and the treatment assembly 48. Mist 82 enters the mist chamber 84 via the mist chamber inlet 96 and leaves the mist chamber 84 via the mist chamber outlet 98. The mist chamber outlet 98 is in fluid communication with the treatment assembly 48 to provide mist 82 to the treatment assembly 48, and can be in direct fluid communication with the cyclone separator 52 or with the dirt collector 54 (see FIG. 2). The mist chamber 84 can optionally further include an ambient air inlet 100 in selective fluid communication with ambient air outside the housing 90 and outside of the vacuum cleaner 40.

The system 76 can further be configured for passive mist dispensing, and can utilize the partial vacuum generated by the suction motor 46 (FIG. 1) in the working air path to draw the mist 82 into the treatment assembly 48. While the suction motor 46 is energized, mist 82 in the mist chamber 84 can be pulled into the treatment assembly 48 by the partial vacuum generated by the suction motor 46.

Optionally, a valve 102 can be provided at the mist chamber outlet 98 between the mist chamber 84 and the treatment assembly 48 for controlling the flow of mist 82 from the mist chamber 84 into the treatment assembly 48. The valve 102 can be 148 configured to be opened temporarily while the suction motor 46 is energized so the mist 82 in the mist chamber 84 can be pulled into the treatment assembly 48 by the partial vacuum generated by the suction motor 46. As a further option, another valve 104 can be provided at the ambient air inlet 100, and is configured to be opened temporarily while the first valve 102 is open to equalize internal and external pressures.

In the illustrated example, the outlet valve 102 normally closing the mist chamber outlet 98 can be an active vent and the inlet valve 104 normally closing the ambient air inlet 100 can be a passive vent. As used herein, an active vent is electrically-powered, while a passive vent is not powered by electricity. The active vent 102 at the mist chamber outlet 98 can include an electrically-controlled valve, such as an electrically controlled solenoid valve. The passive vent 104 at the ambient air inlet 100 can include a mechanical valve, such as a resilient umbrella valve. In another example, instead of the active vent, the mist chamber outlet 98 can be normally closed by a valve configured to be opened by the partial vacuum generated by the suction motor 46. In still another example, instead of the passive vent, the ambient air inlet 100 can be normally closed by an electrically-controlled solenoid valve.

The mist generator 80 can include a piezoelectric transducer 106 and a mist distributor 108, which can include a perforated metal disk configured to be vibrated by the transducer 106. The mist distributor/disk 108 can be provided below the mist chamber inlet 96 to the mist chamber 84. It is noted that, unlike conventional steam generators, the mist generator 80 of the present example atomizes or nebulizes the solution 88 to produce mist 82 and does not heat the solution 88 to a high temperature to produce steam, and therefore does not require as much energy to operate compared to a conventional steam generator. Additionally, the mist generator 80 weighs less than a conventional steam generator, which typically includes a comparatively heavy die cast metal heater block, resulting in reduced handle weight in hand (i.e. the perceived weight of the handle during use). In one example, the mist generator 80 specifically includes a piezoelectric micropump. Other examples of mist generators are also possible.

Figure 4:
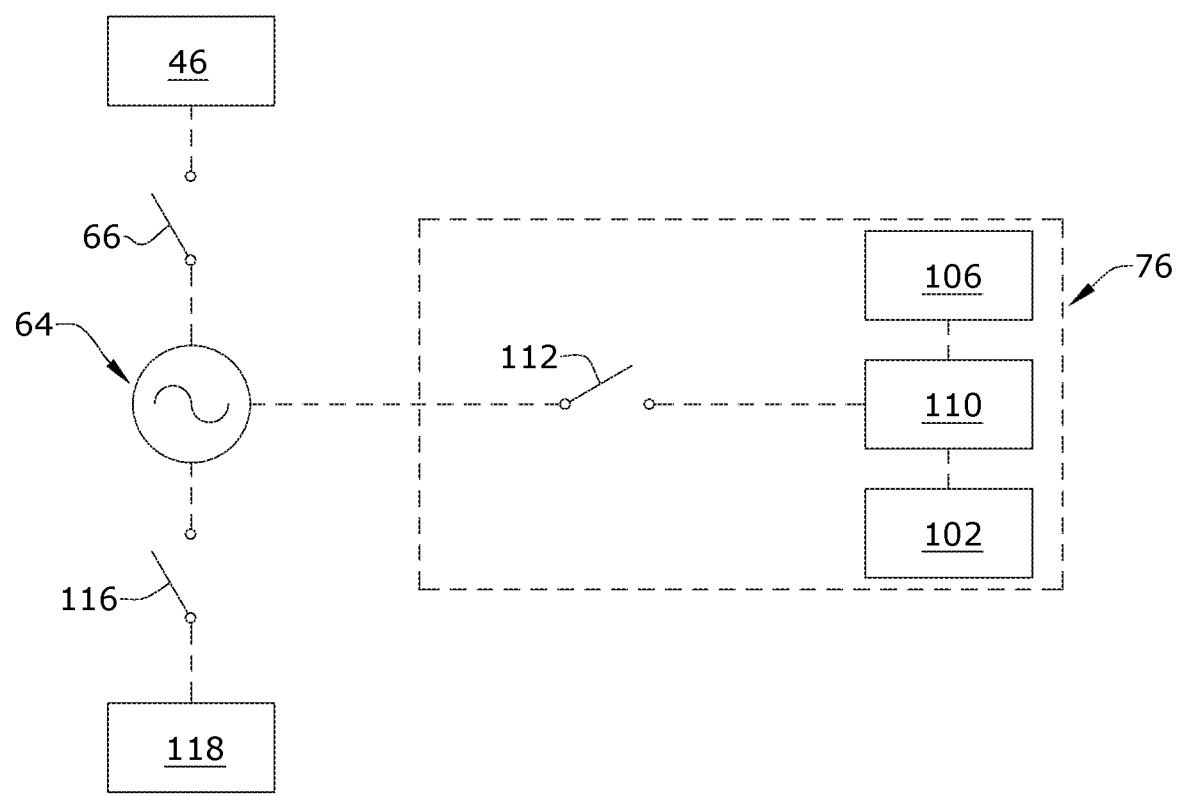
FIG. 4 is one example of an electrical diagram for the system of FIG. 2.

Referring additionally to FIG. 4, in one example of the system 76, the transducer 106 can be connected to an electronic controller 110, such as a printed circuit board (PCB). The electronic controller 110 and transducer 106 can be electrically coupled to the power source 64 of the vacuum cleaner 40. A mist switch 112, including a button or other actuator provided on the housing 90, selectively energizes the electronic controller 110 and transducer 106.

In one example, the system 76 can include an operational cycle for distributing mist 82 into the treatment assembly 48 to neutralize odors and/or abate dust plumes in the treatment assembly 48. The cycle can be initiated before, during or after a vacuum cleaning operation, where a vacuum cleaning operation is an operation where the suction motor 46 is energized to create a working air flow through a working air path of the vacuum cleaner 40. The operational cycle can be controlled by the controller 110. In operation, a user can depress the mist switch 112 to initiate the operational cycle. The controller 110 energizes the transducer 106, which vibrates the mist distributor 108 to generate an atomized solution or mist 82. The mist 82 flows upwardly into the mist chamber 84. Next, the controller 110 emits a signal, which triggers the active vent 102 at the mist chamber outlet 98 to open. The partial vacuum from the treatment assembly 48 draws the mist 82 from the mist chamber 84 through the open outlet 102, and into the treatment assembly 48. The negative pressure inside the treatment assembly 48 also pulls open the passive vent 104, drawing ambient air into the mist chamber 84 through the ambient air inlet 100 as the mist 82 is evacuated into the treatment assembly 48 to equalize pressure.

The transducer 106 can remain energized until the mist switch 112 is pressed again, otherwise a timer can be provided for de-energizing the transducer 106 after a predetermined period of time. It is noted that the transducer 106 can be energized and the active vent 102 opened at the same time, or the active vent 102 can be opened after the transducer 106 has been energized for at least a time suitable for some mist 82 to collect in the mist chamber 84.

With reference to FIG. 2, the odor neutralizer and dust plume abatement system 76 is shown as being on the same side of the vacuum cleaner 40 as a tangential air inlet 114 to the cyclone separator 52, which is in fluid communication with the suction nozzle inlet 70 (FIG. 1), but other locations are possible. Furthermore, the mist switch 112 is shown as being on the same side of the vacuum cleaner 40 as the power switch 66, which can include a button or other actuator provided on the housing of the vacuum cleaner 40, operating the suction motor 46 and an optional agitator switch 116, which can include a button or other actuator provided on the housing of the vacuum cleaner 40, operating an agitator motor 118 (FIG. 4) coupled with the agitator 72 (FIG. 1), which allows for convenient operation of all switches 66, 112, 116 by the same hand of the user, while the other hand of the user may hold on to the vacuum cleaner 40 by the handle grip 62. Other spatial relationships for the switches 66, 112, 116 are also possible.

Figure 5:
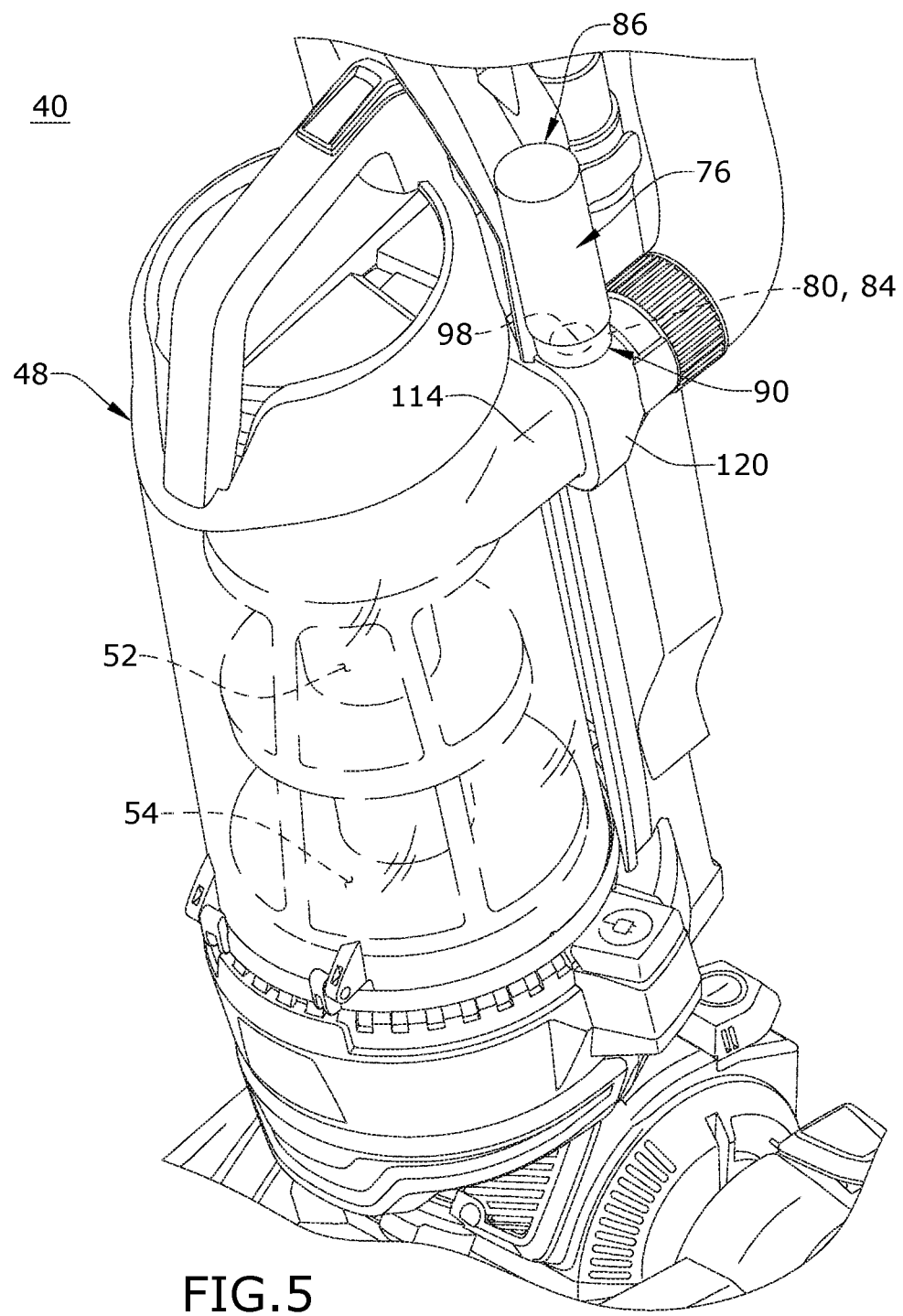
FIG. 5 is a perspective view of a portion of a vacuum cleaner having an odor neutralizer and dust plume abatement system according to another aspect of the present disclosure.

FIG. 5 illustrates another example of the odor neutralizer and dust plume abatement system 76, which may be used with the vacuum cleaner 40 of FIG. 1. The vacuum cleaner 40 may include the same features of the vacuum cleaner 40 of the first example described above with respect to FIG. 1, and is described using the same reference numerals for like elements for the sake of brevity.

The odor neutralizer and dust plume abatement system 76 of FIG. 5 is substantially similar to the system described above with respect to FIGS. 2-3, save for the liquid reservoir 86. In the present example, the liquid reservoir 86 is above the mist generator 80 and mist chamber 84, which are enclosed in the housing 90. As such, a wick within the liquid reservoir 86 can be eliminated and liquid can be provided to the mist generator 80 by gravity feed.

Furthermore, the mist chamber outlet 98 is in fluid communication with the working air path upstream of the treatment assembly 48. As illustrated, the mist chamber outlet 98 is in fluid communication with a conduit 120 which couples with the tangential air inlet 114 to the treatment assembly 48 just upstream of the tangential air inlet 114.

Figure 6:
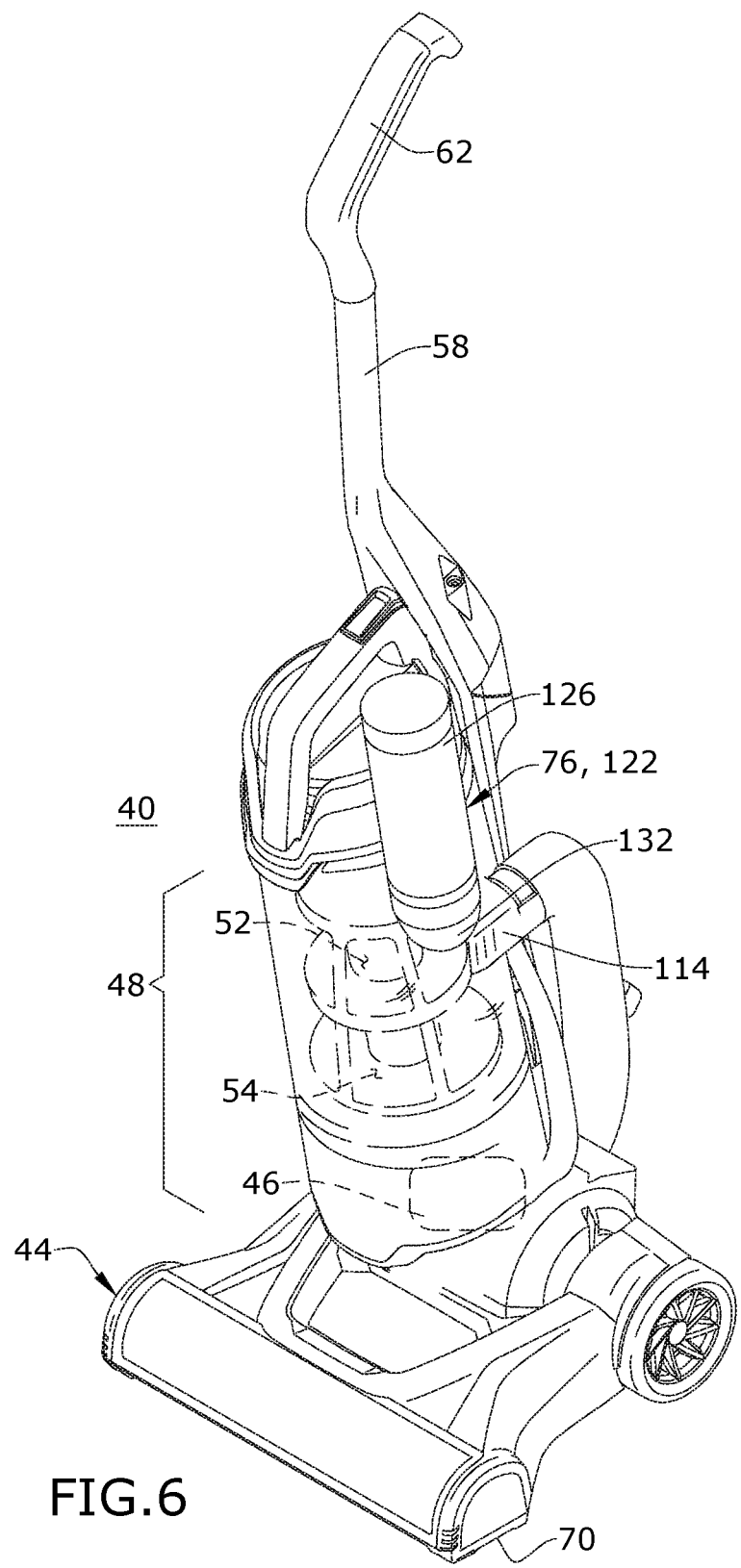
FIG. 6 is a perspective view of a portion of a vacuum cleaner having an odor neutralizer and dust plume abatement system according to another aspect of the present disclosure.
Figure 7:
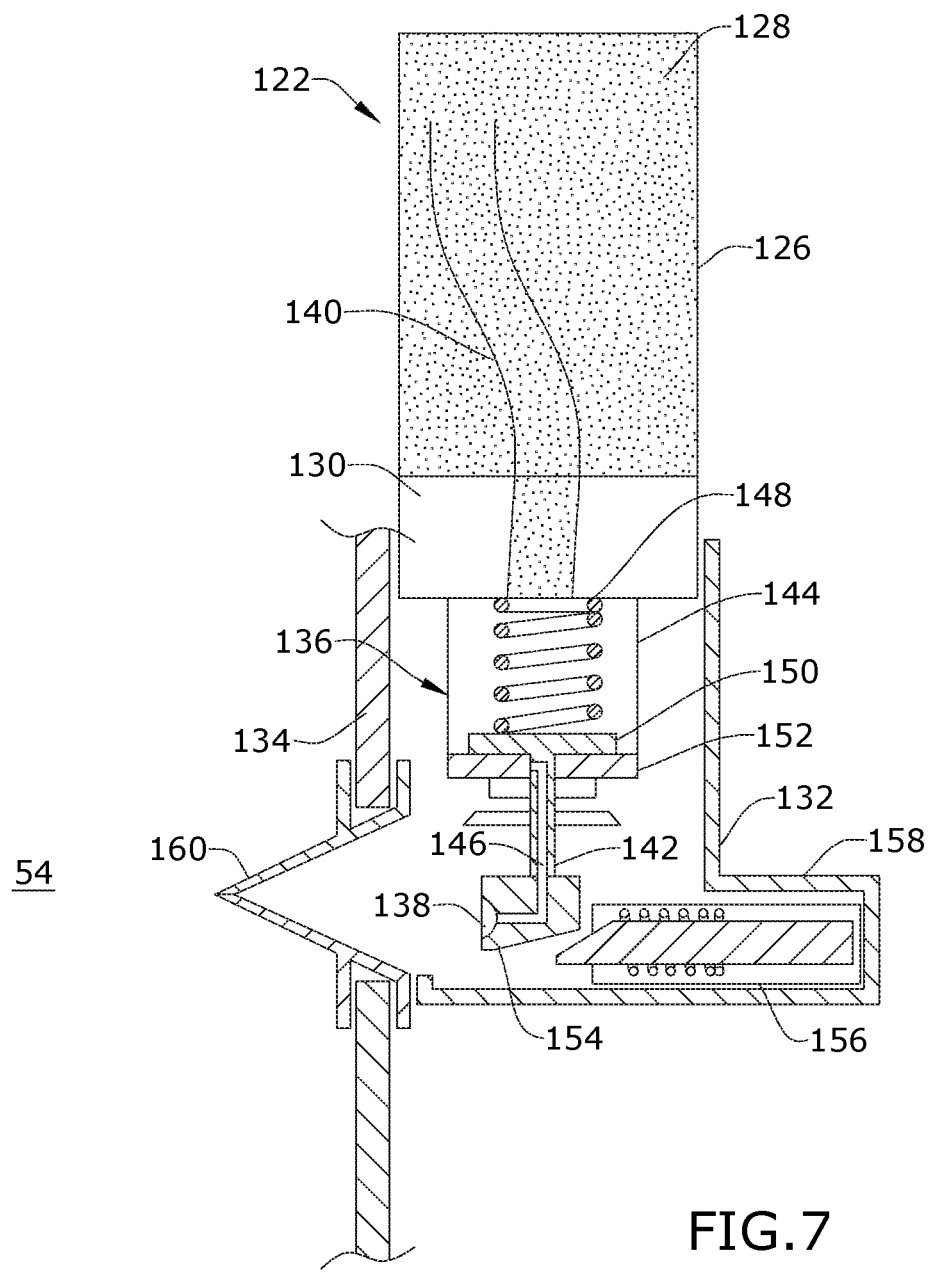
FIG. 7 is a schematic sectional view through a portion of the system of FIG. 6, with a valve in closed position.
Figure 8:
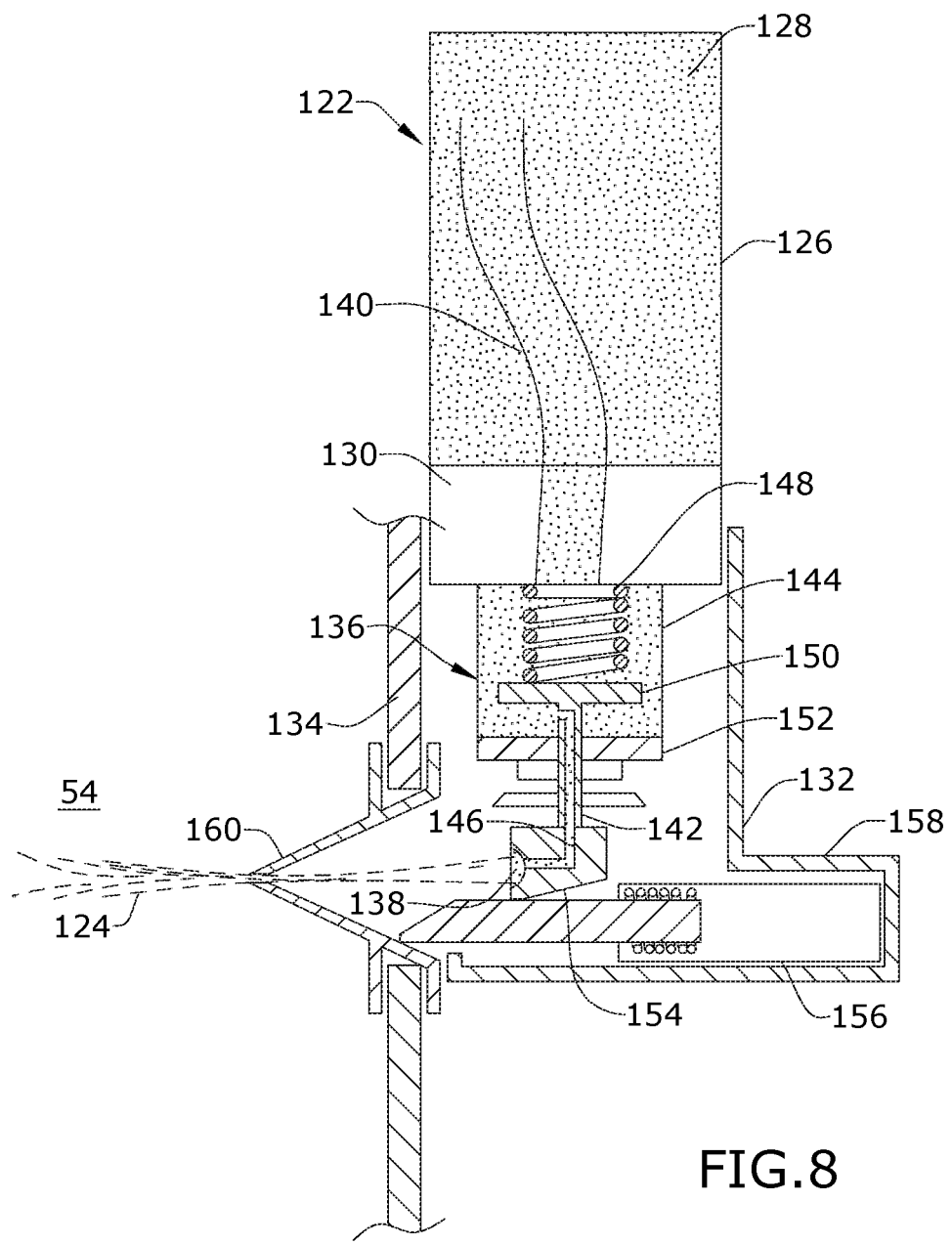
FIG. 8 is a view similar to FIG. 7, with the valve in an open position.

FIGS. 6-8 illustrate another example of the odor neutralizer and dust plume abatement system 76, which may be used with the vacuum cleaner 40 of FIG. 1. The vacuum cleaner 40 may include the same features of the vacuum cleaner 40 of the first example described above with respect to FIG. 1, and is described using the same reference numerals for like elements for the sake of brevity.

The odor neutralizer and dust plume abatement system 76 of FIG. 6 includes an aerosol dispenser 122 in fluid communication with the treatment assembly 48. The system 76 is configured to distribute aerosol mist 124 into the treatment assembly 48 to eliminate or neutralize odors within the treatment assembly 48. The aerosol mist 124 can also agglomerate dust within the dirt collector 54 and reduce dust plumes upon emptying. As illustrated, the aerosol dispenser 122 can be positioned generally above the tangential air inlet 114 to the treatment assembly 48, although other locations are possible.

The system 76 can be configured for active mist dispensing. In one example of active mist dispensing, the system 76 can be configured for a pressurized dispensing of an aerosol mist 124 from the aerosol dispenser 122, such as by using a propellant under pressure. As described in further detail below, the system 76 can be configured to distribute aerosol mist 124 into the treatment assembly 48 automatically after the suction motor 46, generally indicated in phantom line in FIG. 6, is de-energized.

Referring to FIGS. 7-8, the aerosol dispenser 122 includes an aerosol container 126 storing a liquid product 128 and a propellant 130, and a receiver 132 on the vacuum cleaner 40 in fluid communication with the treatment assembly 48 in which the aerosol container 126 is mounted, shown herein as including a compartment formed adjacent a sidewall 134 of the dirt cup 54. The aerosol container 126 can be a disposable or consumable container that is disposed of when empty, and replaced with a new, full container. Alternatively, the aerosol container 126 can be refillable.

The liquid product 128 may be water or a mixture including water and one or more treating agents. Treating agents can include, but are not limited to, odor eliminators, sanitizers, stain removers, odor removers, deodorizers, fragrances, or any combination thereof. In one example, an odor remover solution can include a mixture of polypropylene carbonate, a surfactant and a fragrance.

The aerosol container 126 includes a valve 136 controlling the flow of the pressurized liquid product 128 through an outlet 138 of the container 126. A dip tube 140 is provided in the aerosol container 126 and has one end thereof coupled to the valve 136. The opposite end of the dip tube 140 is free and open. The dip tube 140 conveys a mixture of the product 128 and propellant 130 in the container 126 to the valve 136. The outlet 138 is configured to break up the mixture of liquid product 128 and propellant 130 into a fine spray of aerosol mist 124.

The valve 136 includes a valve plunger or valve stem 142 slidingly received by a valve housing 144. The valve stem 142 includes a channel 146 in fluid communication with the outlet 138. A spring 148 biases the valve 136 toward a closed position shown in FIG. 7 by pushing the valve stem 142 downwardly to close an inlet to the channel 146. In the illustrated example, a spring cup 150 is provided at one end of the valve stem 142, and the spring 148 pushes the spring cup 150 against a gasket 152 to close the inlet to the channel 146.

An actuator head 154 is coupled with the valve 136, and in particular the valve stem 142, and includes the outlet 138. The actuator head 154 is depressible, and an actuator 156 selectively depresses the actuator head 154 to open the valve 136. A housing 158 for the actuator 156 can be coupled with the receiver 132 for the aerosol container 126, such that when the aerosol container 126 is mounted in the receiver 132, the actuator 156 is in register with the actuator head 154. In one example, as shown herein, the actuator 156 can be an electrically controlled solenoid valve. In one example, the solenoid actuator 156 is connected to a thermal switch that senses temperature of the suction motor 46. The thermal switch is configured to open and close at predetermined temperature limits. In another example, the actuator 156 can be a manually-controllable actuator and the user can selectively dispense aerosol mist 124 as desired. Alternatively, the actuator 156 can be eliminated and the valve 136 can be actuated manually by pressing the aerosol container 126.

When the actuator head 154 is depressed as shown in FIG. 8, the valve stem 142 moves and the inlet to the channel 146 slides away from the gasket 152, opening a passage to the outlet 138. The high-pressure propellant 130 drives the liquid product 128 through the dip tube 140 and channel 146, and out through the outlet 138. The outlet 138 serves to atomize or break up the mixture into a fine spray of aerosol mist 124.

The outlet 138 of the aerosol dispenser 122 is fluidly connected with an aerosol inlet on the dirt cup 54 when the aerosol container 126 is mounted in the receiver 132. A displaceable seal 160 can be provided at the aerosol inlet on the dirt cup 54 and can be normally closed to prevent air leaks when the aerosol container 126 is mounted in the receiver 132. The seal 160 is configured to open at a predetermined pressure, such as at or below the pressure of the aerosol mist 124 as shown in FIG. 8 to deliver the mist to the dirt cup 54.

Figure 9:
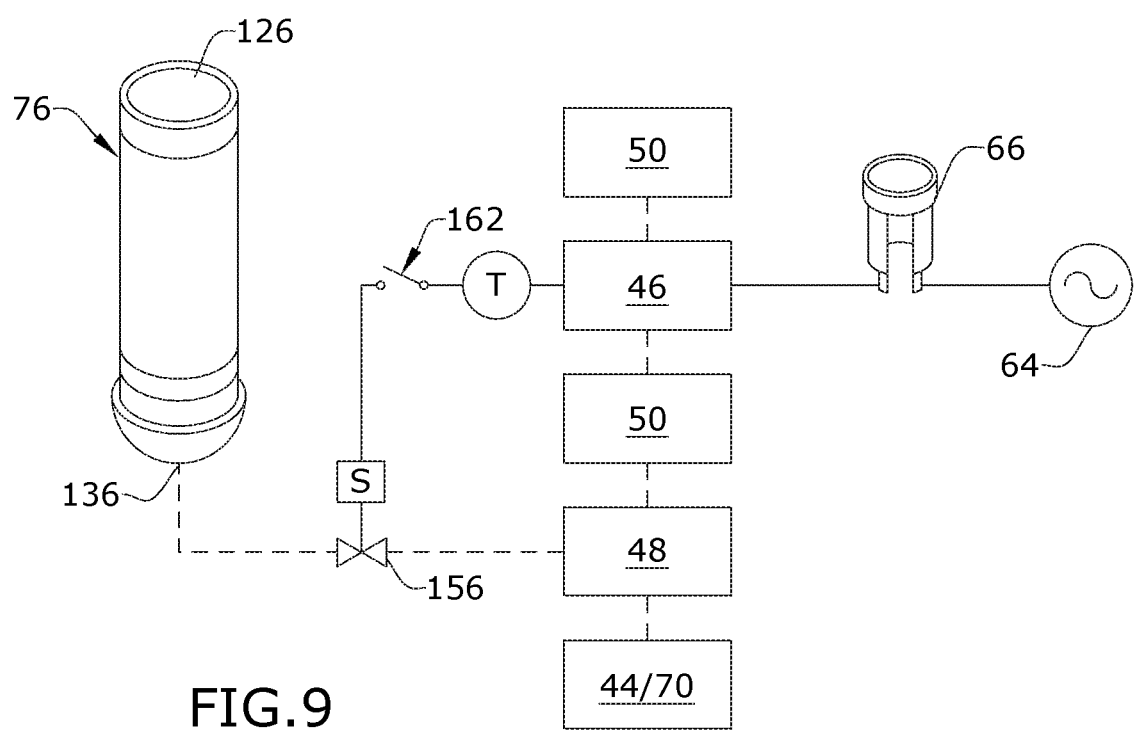
FIG. 9 is one example of a working airflow and electrical diagram for the system of FIG. 6.

Referring to FIG. 9, in one example, the system 76 can be electrically coupled to the power source 64 of the vacuum cleaner 40 as shown, or to its own separate supply of power, such as a battery. In the example of the system 76 shown in FIG. 9, the actuator 156 is an electrically controlled solenoid valve and is connected to a thermal switch 162 that senses temperature of the suction motor 46. The thermal switch 162 is configured to open and close at predetermined temperature limits.

During normal operation, the suction motor 46 heats up and when the vacuum cleaner 40 is powered off, heat from the suction motor 46 is transferred to its surroundings, including ambient air and other components in contact with the suction motor 46 through conduction, convection and radiation. When the motor temperature reduces to a predetermined threshold value, the thermal switch 162 closes and delivers power to the solenoid actuator 156, which opens the valve 136 and distributes atomized mist into the treatment assembly 48, and specifically into the dirt cup 54.

Figure 10:
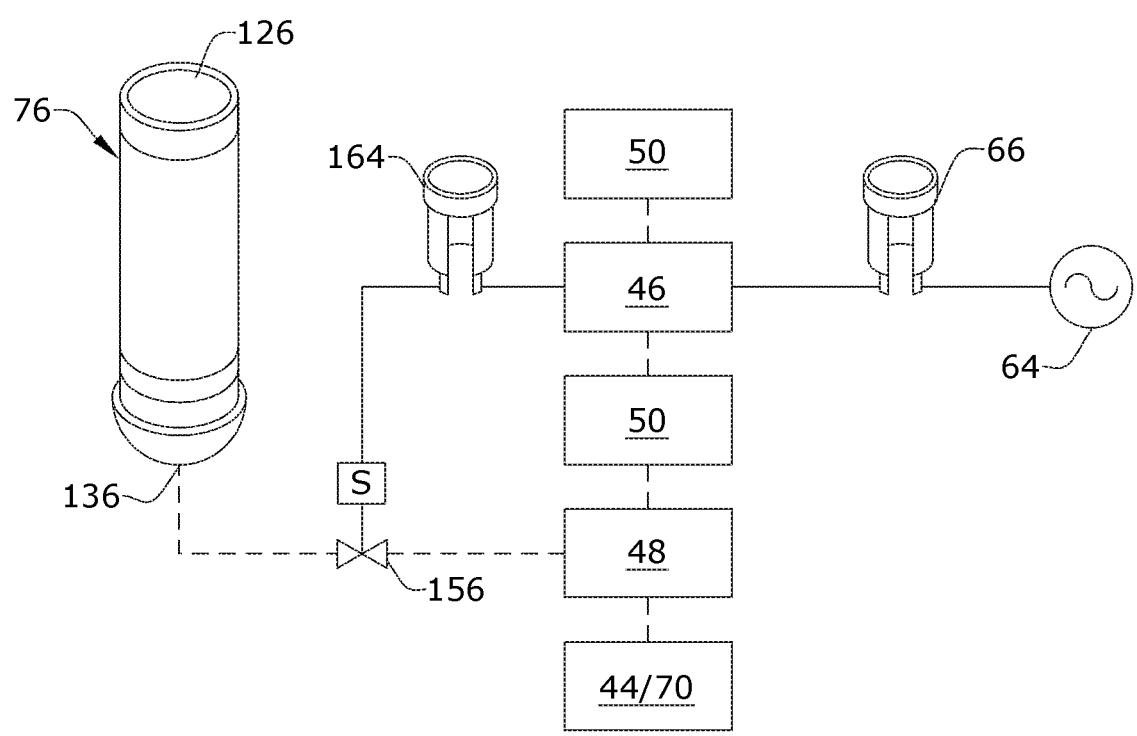
FIG. 10 is another example of a working airflow and electrical diagram for the system of FIG. 6.

Referring to FIG. 10, in another example, the system 76 can be electrically coupled to the power source 64 of the vacuum cleaner 40 as shown, or to its own separate supply of power, such as a battery. In the example of the system 76 shown in FIG. 10 the actuator 156 is an electrically controlled solenoid valve and is connected to a manual actuator switch 164. The valve 136 can be opened by manually pressing the actuator switch 164. The valve 136 may remain open until the actuator switch 164 is pressed again.

It is noted that while examples of a combined odor neutralizer and dust plume abatement system for a vacuum cleaner are described herein, in other aspects of the present disclosure, a system configured to neutralize odors alone or abate dust plumes alone can be provided using at least some of the system elements described herein.

To the extent not already described, the different features and structures of the various examples of the vacuum cleaner 40 and/or odor neutralizer and dust plume abatement system 76 may be used in combination with each other as desired. That one feature may not be illustrated in all of the examples of the vacuum cleaner 40 and/or odor neutralizer and dust plume abatement system 76 is not meant to be construed that it cannot be, but is done for brevity of description. Thus, the various features of the different examples of vacuum cleaner 40 and/or odor neutralizer and dust plume abatement system 76 may be mixed and matched as desired to form new examples, whether or not the new examples are expressly described.

Furthermore, while the vacuum cleaner shown herein is an upright or stick-type vacuum cleaner, at least some aspects of the present disclosure, not illustrated herein, can be used in a vacuum cleaner configured as a canister vacuum cleaner, a vacuum cleaner having a detachable pod with a hand-carried mode of operation, a hand-held vacuum cleaner, or an autonomous robotic vacuum cleaner. Still further, the vacuum cleaner can additionally have fluid delivery capability, including applying liquid or steam to the surface to be cleaned, and/or fluid extraction capability.

While the present disclosure has been specifically described in connection with certain specific examples thereof, it is to be understood that this is by way of illustration and not of limitation. Reasonable variation and modification are possible with the scope of the foregoing disclosure and drawings without departing from the spirit of the invention which, is defined in the appended claims.

Hence, specific dimensions and other physical characteristics relating to the embodiments disclosed herein are not to be considered as limiting, unless the claims expressly state otherwise.

The invention claimed is:

1. A surface cleaning apparatus, comprising:
   a housing;
   a working air path through the housing comprising a dirty air inlet and a clean air outlet;
   a working air treatment assembly defining a portion of the working air path, the working air treatment assembly comprising:
      a cyclone separator,
      a dirt cup configured to receive and collect contaminants separated by the cyclone separator, the dirt cup further comprising an aerosol inlet, and
      a displaceable seal provided at the aerosol inlet on the dirt cup with the displaceable seal in a normally closed position, wherein the displaceable seal is adapted to open at a predetermined pressure, and
   a suction source defining a portion of the working air path and in fluid communication with the working air treatment assembly; and
   an odor neutralizer and dust plume abatement system configured to dispense a mist into the working air path and including a receiver including a mount for receiving an aerosol dispenser, the receiver in fluid communication with the working air path at or upstream of the working air treatment assembly via the aerosol inlet.

2. The surface cleaning apparatus of claim 1 wherein the working air treatment assembly comprises a tangential air inlet.

3. The surface cleaning apparatus of claim 2 wherein the aerosol dispenser is provided above the tangential air inlet.

4. The surface cleaning apparatus of claim 1 wherein the receiver further comprises a compartment formed adjacent a sidewall of the dirt cup.

5. The surface cleaning apparatus of claim 1, further comprising the aerosol dispenser configured to be received within the mount and adapted to provide an aerosol mist to the working air path.

6. The surface cleaning apparatus of claim 5 wherein the aerosol dispenser further comprises a container with a propellant.

7. The surface cleaning apparatus of claim 6 wherein the aerosol dispenser is a disposable container or a consumable container and the mount is configured to selectively receive the aerosol dispenser.

8. The surface cleaning apparatus of claim 5 wherein the aerosol dispenser is refillable and the mount is configured to permanently retain at least a portion of the aerosol dispenser.

9. The surface cleaning apparatus of claim 5, further comprising a valve adapted to control a flow of the aerosol mist to the working air path and wherein the valve is normally closed.

10. The surface cleaning apparatus of claim 9, further comprising an actuation system including an actuator that is operably coupled to the valve and adapted to move the valve between a closed position and an opened position.

11. The surface cleaning apparatus of claim 10, further comprising:
   a power source, wherein the suction source and the valve are electrically coupled to the power source;
   a power switch disposed between the suction source and the power source; and an actuator switch disposed between the valve and the power source the actuator switch, separate from the power switch on the housing.

12. The surface cleaning apparatus of claim 10 wherein the actuator is a manually-controllable actuator.

13. The surface cleaning apparatus of claim 1 wherein the housing comprises a base adapted to be moved over a surface to be cleaned and an upper unit coupled with the base, wherein the dirty air inlet is defined by a suction nozzle inlet in the base and the clean air outlet is defined by an exhaust opening in the housing downstream of the suction source.

14. The surface cleaning apparatus of claim 1 wherein the working air treatment assembly is removable from the housing and the odor neutralizer and dust plume abatement system is integral with the working air treatment assembly, such that when the working air treatment assembly is removed from the housing, the odor neutralizer and dust plume abatement system is also removed.

15. A surface cleaning apparatus, comprising:
a housing;
a working air path through the housing comprising a dirty air inlet and a clean air outlet;
a working air treatment assembly defining a portion of the working air path;
a suction source defining a portion of the working air path and in fluid communication with the working air treatment assembly;
an odor neutralizer and dust plume abatement system configured to dispense an aerosol mist into the working air path and including a receiver including a mount for receiving an aerosol dispenser, the receiver in fluid communication with the working air path at or upstream of the working air treatment assembly;
a valve adapted to control a flow of the aerosol mist to the working air path, wherein the valve is normally closed; and
an actuation system including an actuator that is operably coupled to the valve and adapted to move the valve between a closed position and an opened position and operably connected to a thermal switch indicative of a temperature of the suction source and the thermal switch is configured to open and close at predetermined temperature limits.

16. The surface cleaning apparatus of claim 15 wherein the working air treatment assembly comprises a cyclone separator and a dirt cup configured to receive and collect contaminants separated by the cyclone separator.

17. The surface cleaning apparatus of claim 16 wherein the dirt cup further comprises an aerosol inlet.

18. The surface cleaning apparatus of claim 17, further comprising a displaceable seal provided at the aerosol inlet on the dirt cup with the displaceable seal in a normally closed position.

19. The surface cleaning apparatus of claim 18 wherein the displaceable seal is adapted to open at a predetermined pressure.

20. The surface cleaning apparatus of claim 15 wherein the actuator is an electrically controlled solenoid valve.

* * * * *